(12) United States Patent
Millard

(10) Patent No.: US 9,938,308 B2
(45) Date of Patent: Apr. 10, 2018

(54) COORDINATION COMPOUNDS HAVING REDOX NON-INNOCENT LIGANDS AND FLOW BATTERIES CONTAINING THE SAME

(71) Applicant: LOCKHEED MARTIN ADVANCED ENERGY STORAGE, LLC, Bethesda, MD (US)

(72) Inventor: Matthew Millard, Cambridge, MA (US)

(73) Assignee: Lockheed Martin Energy, LLC, Bethesda, MD (US)

(*) Notice: Subject to any disclaimer, the term of this patent is extended or adjusted under 35 U.S.C. 154(b) by 0 days.

(21) Appl. No.: 15/093,606

(22) Filed: Apr. 7, 2016

(65) Prior Publication Data

US 2017/0291916 A1    Oct. 12, 2017

(51) Int. Cl.
C07F 7/28 (2006.01)
H01M 8/18 (2006.01)
H01M 8/20 (2006.01)

(52) U.S. Cl.
CPC .............. C07F 7/28 (2013.01); H01M 8/188 (2013.01); H01M 8/20 (2013.01); Y02E 60/528 (2013.01)

(58) Field of Classification Search
CPC ............ C07F 7/28; H01M 8/188; H01M 8/20
See application file for complete search history.

(56) References Cited

U.S. PATENT DOCUMENTS

| 1,279,295 A | 9/1918 | Downs |
| 2,353,782 A | 7/1944 | Neumark |

(Continued)

FOREIGN PATENT DOCUMENTS

| CN | 1284208 A | 2/2001 |
| CN | 101877412 A | 11/2010 |

(Continued)

OTHER PUBLICATIONS

Borgias, "Synthetic, structural, and physical studies of titanium complexes of catechol and 3,5-di-tert-butylcatechol," Inorg. Chem., Apr. 1984, 23(8), 1009-1016.

(Continued)

*Primary Examiner* — Stewart A Fraser
(74) *Attorney, Agent, or Firm* — McDermott Will & Emery LLP

(57) ABSTRACT

Electrolyte solutions for flow batteries and other electrochemical systems can contain an active material capable of transferring more than one electron per oxidation-reduction cycle. Such active materials can include coordination compounds containing a metal center and at least one redox non-innocent ligand. Accordingly, flow batteries can include a first half-cell having a first electrolyte solution therein, where the first electrolyte solution contains a coordination compound having at least one redox non-innocent ligand coordinated to a metal center. Particular redox non-innocent ligands can include those bearing a quinone functional group, such as substituted catecholates bearing a quinone functional group. Some active materials can include compositions containing a coordination compound having at least one redox non-innocent ligand coordinated to a metal center, where the at least one redox non-innocent ligand is a substituted catecholate or a salt thereof bearing a quinone functional group.

15 Claims, 1 Drawing Sheet

(56) References Cited

U.S. PATENT DOCUMENTS

| | | |
|---|---|---|
| 2,415,792 A | 2/1947 | Gravell |
| 3,294,588 A | 12/1966 | Morton |
| 3,425,796 A | 2/1969 | Bauer |
| 3,428,654 A | 2/1969 | Rubinfeld |
| 3,573,984 A | 4/1971 | Shah |
| 3,707,449 A | 12/1972 | Reinhardt et al. |
| 3,772,379 A | 11/1973 | Woodgate |
| 3,801,642 A | 4/1974 | Worrel |
| 3,876,435 A | 4/1975 | Dollman |
| 3,916,004 A | 10/1975 | Okada et al. |
| 3,919,000 A | 11/1975 | Yarrington |
| 3,920,756 A | 11/1975 | Tahara et al. |
| 3,929,506 A | 12/1975 | Leddy et al. |
| 3,985,517 A | 10/1976 | Johnson |
| 3,985,585 A | 10/1976 | Tuttle et al. |
| 4,046,861 A | 9/1977 | Reinhardt et al. |
| 4,064,324 A | 12/1977 | Eustace |
| 4,069,371 A | 1/1978 | Zito |
| 4,126,529 A | 11/1978 | DeBerry |
| 4,180,623 A | 12/1979 | Adams |
| 4,202,799 A | 5/1980 | Yoshimura et al. |
| 4,233,144 A | 11/1980 | Pace et al. |
| 4,362,791 A | 12/1982 | Kaneko et al. |
| 4,378,995 A | 4/1983 | Gratzfeld et al. |
| 4,410,606 A | 10/1983 | Loutfy et al. |
| 4,436,711 A | 3/1984 | Olson |
| 4,436,712 A | 3/1984 | Olson |
| 4,436,713 A | 3/1984 | Olson |
| 4,436,714 A | 3/1984 | Olson |
| 4,443,423 A | 4/1984 | Olson |
| 4,443,424 A | 4/1984 | Olson |
| 4,468,441 A | 8/1984 | D'Agostino et al. |
| 4,485,154 A | 11/1984 | Remick et al. |
| 4,520,083 A | 5/1985 | Prater et al. |
| 4,563,403 A | 1/1986 | Julian |
| 4,592,973 A | 6/1986 | Pemsler et al. |
| 4,617,244 A | 10/1986 | Greene |
| 4,680,308 A | 7/1987 | Schwartz et al. |
| 4,818,646 A | 4/1989 | Takakubo et al. |
| 4,880,758 A | 11/1989 | Heistand, II et al. |
| 4,952,289 A | 8/1990 | Ciccone et al. |
| 4,959,135 A | 9/1990 | Zenner et al. |
| 4,973,720 A | 11/1990 | Saito et al. |
| 5,084,533 A | 1/1992 | Shah et al. |
| 5,102,906 A | 4/1992 | Nakayama et al. |
| 5,122,461 A | 6/1992 | Hsiung et al. |
| 5,264,097 A | 11/1993 | Vaughan |
| 5,302,481 A | 4/1994 | Ong |
| 5,318,865 A | 6/1994 | Kaneko et al. |
| 5,433,934 A | 7/1995 | Chang et al. |
| 5,472,807 A | 12/1995 | Licht et al. |
| 5,643,670 A | 7/1997 | Chung |
| 5,679,239 A | 10/1997 | Blum et al. |
| 5,759,711 A | 6/1998 | Miyabayashi et al. |
| 5,785,841 A | 7/1998 | Tseng |
| 5,876,581 A | 3/1999 | Itaya et al. |
| 5,910,366 A | 6/1999 | Chowdhury et al. |
| 6,001,326 A | 12/1999 | Kim et al. |
| 6,030,517 A | 2/2000 | Lincot et al. |
| 6,054,230 A | 4/2000 | Kato |
| 6,461,772 B1 | 10/2002 | Miyake et al. |
| 6,475,661 B1 | 11/2002 | Pellegri et al. |
| 6,485,868 B1 | 11/2002 | Tsujioka et al. |
| 6,555,989 B1 | 4/2003 | Pearson |
| 6,585,951 B1 | 7/2003 | Hong et al. |
| 6,624,328 B1 | 9/2003 | Guerra |
| 7,046,418 B2 | 5/2006 | Lin et al. |
| 7,193,764 B2 | 3/2007 | Lin et al. |
| 7,223,833 B1* | 5/2007 | Nielsen .............. C07K 14/003 435/455 |
| 7,252,905 B2 | 8/2007 | Clarke et al. |
| 7,265,162 B2 | 9/2007 | Yandrasits et al. |
| 7,348,088 B2 | 3/2008 | Hamrock et al. |
| 7,463,917 B2 | 12/2008 | Martinez |
| 7,508,568 B2 | 3/2009 | Lin et al. |
| 7,550,231 B2 | 6/2009 | Stauffer |
| 7,557,164 B2 | 7/2009 | Felix et al. |
| 7,625,663 B2 | 12/2009 | Clarke et al. |
| 7,645,540 B2 | 1/2010 | Boone et al. |
| 7,678,728 B2 | 3/2010 | Olson et al. |
| 7,745,056 B2 | 6/2010 | Lee et al. |
| 7,767,777 B2 | 8/2010 | Buesing et al. |
| 7,927,731 B2 | 4/2011 | Sahu |
| 7,931,981 B2 | 4/2011 | Boone et al. |
| 7,935,366 B2 | 5/2011 | Pahuja et al. |
| 7,998,335 B2 | 8/2011 | Feeney et al. |
| 8,129,554 B2 | 3/2012 | Schwaiger |
| 8,187,441 B2 | 5/2012 | Evans et al. |
| 8,445,118 B2 | 5/2013 | Cordonier et al. |
| 8,492,581 B2 | 7/2013 | Frost et al. |
| 8,691,413 B2 | 4/2014 | Esswein et al. |
| 8,753,761 B2 | 6/2014 | Esswein et al. |
| 9,300,000 B2 | 3/2016 | Jansen et al. |
| 9,382,274 B2 | 7/2016 | Esswein et al. |
| 9,409,842 B1 | 8/2016 | Fu et al. |
| 2002/0177042 A1 | 11/2002 | Amendola |
| 2003/0068561 A1 | 4/2003 | Okahara et al. |
| 2003/0143456 A1 | 7/2003 | Kazacos et al. |
| 2003/0228394 A1 | 12/2003 | Abdel-Monem et al. |
| 2004/0096746 A1 | 5/2004 | Wietelmann et al. |
| 2005/0098437 A1 | 5/2005 | Shiepe |
| 2005/0244707 A1 | 11/2005 | Skyllas-Kazacos et al. |
| 2006/0047094 A1 | 3/2006 | Cherkasov et al. |
| 2007/0275291 A1 | 11/2007 | Gu et al. |
| 2008/0274385 A1 | 11/2008 | Creeth |
| 2008/0292964 A1 | 11/2008 | Kazacos et al. |
| 2009/0110998 A1 | 4/2009 | Miyachi et al. |
| 2009/0130525 A1 | 5/2009 | Miyachi et al. |
| 2009/0208807 A1 | 8/2009 | Miyachi et al. |
| 2009/0308752 A1 | 12/2009 | Evans et al. |
| 2010/0003586 A1 | 1/2010 | Sahu |
| 2010/0059388 A1 | 3/2010 | Clarke et al. |
| 2010/0086823 A1 | 4/2010 | Koshino et al. |
| 2010/0086983 A1 | 4/2010 | Gellett et al. |
| 2010/0239946 A1 | 9/2010 | Miyachi et al. |
| 2011/0014532 A1 | 1/2011 | Knuckey et al. |
| 2011/0136016 A1 | 6/2011 | Huang et al. |
| 2011/0189549 A1 | 8/2011 | Sun et al. |
| 2011/0195283 A1 | 8/2011 | Sun et al. |
| 2011/0200890 A1 | 8/2011 | Kocherginsky |
| 2011/0223450 A1 | 9/2011 | Horne et al. |
| 2011/0244277 A1 | 10/2011 | Gordon, II et al. |
| 2011/0244367 A1 | 10/2011 | Watahiki et al. |
| 2012/0052347 A1 | 3/2012 | Wilson et al. |
| 2012/0077095 A1 | 3/2012 | Roumi et al. |
| 2012/0107661 A1 | 5/2012 | Lee et al. |
| 2012/0135278 A1 | 5/2012 | Yoshie et al. |
| 2012/0171541 A1 | 7/2012 | Park et al. |
| 2012/0183868 A1 | 7/2012 | Toussaint et al. |
| 2012/0196188 A1 | 8/2012 | Zhang et al. |
| 2012/0202099 A1 | 8/2012 | Perry et al. |
| 2012/0208061 A1 | 8/2012 | Sahu et al. |
| 2012/0244406 A1 | 9/2012 | Xia et al. |
| 2012/0263990 A1 | 10/2012 | Kim |
| 2013/0004819 A1 | 1/2013 | Mun et al. |
| 2013/0157087 A1 | 6/2013 | Pandy et al. |
| 2013/0252062 A1 | 9/2013 | Wilkins et al. |
| 2013/0252137 A1 | 9/2013 | Zhang et al. |
| 2014/0028260 A1 | 1/2014 | Goeltz et al. |
| 2014/0028261 A1 | 1/2014 | Esswein et al. |
| 2014/0030572 A1* | 1/2014 | Esswein ............ H01M 10/4242 429/107 |
| 2014/0030573 A1* | 1/2014 | Esswein ............ H01M 10/4242 429/107 |
| 2014/0030631 A1* | 1/2014 | Esswein ................ H01M 8/188 429/499 |
| 2014/0051003 A1 | 2/2014 | Esswein et al. |
| 2014/0080035 A1 | 3/2014 | Esswein et al. |
| 2014/0138576 A1* | 5/2014 | Esswein .................. C07F 7/28 252/182.1 |
| 2014/0178735 A1 | 6/2014 | Wang et al. |
| 2014/0193687 A1 | 7/2014 | Park et al. |
| 2014/0239906 A1 | 8/2014 | Anderson et al. |
| 2014/0274936 A1 | 9/2014 | Piccariello et al. |

(56) References Cited

U.S. PATENT DOCUMENTS

| | | | |
|---|---|---|---|
| 2014/0349177 A1 | 11/2014 | Chung et al. | |
| 2014/0377666 A1 | 12/2014 | Kodama et al. | |
| 2015/0236543 A1 | 8/2015 | Brushett et al. | |
| 2015/0372333 A1 | 12/2015 | Odom et al. | |
| 2016/0066578 A1 | 3/2016 | Ala'Aldeen et al. | |
| 2016/0149251 A1* | 5/2016 | Reece | H01M 8/188 429/105 |
| 2016/0208165 A1 | 7/2016 | Li et al. | |
| 2016/0264603 A1 | 9/2016 | Esswein et al. | |
| 2016/0268623 A1 | 9/2016 | Esswein et al. | |
| 2016/0272659 A1 | 9/2016 | King et al. | |
| 2016/0276693 A1 | 9/2016 | Goeltz et al. | |
| 2016/0276694 A1 | 9/2016 | Goeltz et al. | |
| 2016/0276695 A1 | 9/2016 | Esswein et al. | |
| 2017/0253620 A1 | 9/2017 | Humbarger et al. | |
| 2017/0256811 A1 | 9/2017 | Humbarger et al. | |
| 2017/0271704 A1 | 9/2017 | Morris-Cohen | |

FOREIGN PATENT DOCUMENTS

| | | |
|---|---|---|
| EP | 0814527 A2 | 12/1997 |
| EP | 1290068 A2 | 3/2003 |
| EP | 1411576 A1 | 4/2004 |
| EP | 1901379 A1 | 3/2008 |
| EP | 2235781 A1 | 10/2010 |
| EP | 2463950 A1 | 6/2012 |
| FR | 1533662 A | 7/1968 |
| GB | 1354886 A | 6/1974 |
| WO | WO-95/12219 A1 | 5/1995 |
| WO | WO-1997/017354 A1 | 5/1997 |
| WO | WO-2004/095602 A2 | 11/2004 |
| WO | WO-2006/135958 A1 | 12/2006 |
| WO | WO-2007/044852 A2 | 4/2007 |
| WO | WO-2007/101284 A1 | 9/2007 |
| WO | WO-2011/075135 A1 | 6/2011 |
| WO | WO-2011/098781 A1 | 8/2011 |
| WO | WO-2011/149624 A1 | 12/2011 |
| WO | WO-2012/075810 A1 | 6/2012 |
| WO | WO-2013/006427 A1 | 1/2013 |
| WO | WO-2013/048603 A1 | 4/2013 |
| WO | WO-2015/069439 A1 | 5/2015 |

OTHER PUBLICATIONS

Brezina, "Study of the reduction of oxygen on a carbon paste electrode in an alkaline medium," Coll. Czech. Chem. Commun., 1973, 38(10), 3024-3031.
Caulton, "Systematics and Future Projections Concerning Redox-Noninnocent Amide/Imine Ligands," Eur. J. Inorg. Chem., Jan. 2012, 2012(3), 435-443.
Cerofontain et al. "Sulfonation and sulfation on reaction of 1,2-dihydroxybenzene and its methyl ethers in concentrated aqueous sulfuric acid," Recl Tray Chim Pays-Bas, 1988, pp. 325-330, vol. 107.
Chen, "Solution Redox Couples for Electrochemical Energy Storage: I. Iron (III)-Iron (II) Complexes with O-Phenanthroline and Related Ligands," Journal of the Electrochemical Society, Jul. 1981, 128(7), 1460-1467.
Cohen, "The Association offerrocyanide Ions With Various Cations," J. Phys, Chem., Aug. 1957, 61(8), 1096-1100.
Davies, "Eiectroceramics from Source Materials via Molecular Intermediates: PbTi03 from Ti02 via [Ti(catecholate)3]2-," J. Am. Ceram. Soc., Aug. 1990, 73(8), 2570-2572.
Dehaen et al, "A Self-Assembled Complex with a Titanium (IV) Catecholate Core as a Potential Bimodal Contrast Agent," Chem Eur J, 2012, pp. 293-302, vol. 18.
Fryda, "Wastewater Treatment With Diamond Electrodes," Diamond Materials, Electrochemical Society Proceedings, 2000, 99(32), 473-483.
Gail, "Cyano Compounds, Inorganic" in Ullmann's Encyclopedia of Industrial Chemistry, 2012, 10, 674-710.
Hollandsworth, "Zinc/Ferrocyanide Battery Development Phase IV" Lockheed Missiles and Space Company, Inc., Contractor report, Sandia Contract DE-AC04-760P00789, May 1985, 278 pages.
Kim, "Novel catalytic effects of Mn304 for all vanadium redox flow batteries," Chem. Commun., Apr. 2012, 48(44), 5455-5457.
Kulesza, "Electrochemical preparation and characterization of hybrid films composed of Prussian blue type metal hexacyanoferrate and conducting polymer," Electrochimica Acta, Aug. 2001, 46(26-27), 4065-4073.
Leung, "Development of A Zinc—Cerium Redox Flow Battery", 2011, 352 pages.
Leung, "An undivided zinc—cerium zinccerium redox flow batteryoperating at room temperature (295 K)," Electrochemistry Communications, 2011, vol. 13, pp. 770-773.
Leung, "Ce(III)/Ce(iV) in methanesulfonic acid as the positive half cell of a redox flow battery," Electrochimica Acta, 2011, vol. 56, pp. 2145-2153.
Leung, "Zinc deposition and dissolution in methanesulfonic acid onto a carbon composite electrode as the negative electrode reactions in a hybrid redox flow battery," Electrochimica Acta, 2011, vol. 56, pp. 6536-6546.
Leung, "Characterization of a zinc—cerium flow battery," Journal of Power Sources, 2011, vol. 195, pp. 5174-5185.
Modiba, "Electrochemical impedance spectroscopy study of Ce(IV) with aminopolycarboxylate ligands for redox flow batteries applications," Journal of Power Sources, May 2012, vol. 205, 1-9.
Modiba, "Electrochemical study of cerium(IV) in the presence of ethylenediaminetetraacetic acid (EDTA) and diethylenetriaminepentaacetate (DTPA) ligands," Journal of Applied Electrochemistry, Sep. 2008, 38(9), 1293-1299.
Modiba, "Electrolytes for redox flow battery systems," Dissertation presented for the degree of Doctor of Philosophy Chemistry at the University of Stellenbosch, Department of Chemistry and Polymer Science, Mar. 2010.
Nguyen, "Flow Batteries," The Electrochemical Society Interface, Fall2010, 19(3), 54-56.
Pharr, "Infrared Spectroelectrochemical Analysis of Adsorbed Hexacyanoferrate Species Formed during Potential Cycling in the Ferrocyanide/Ferricyanide Redox Couple," Anal. Chem., Nov. 1997, 69(22), 4673-4679.
Raymond, "Coordination isomers of biological iron transport compounds. VI. Models of the enterobactin coordination site. A crystal field effect in the structure of potassium tris ( catecholato )chromate( III) and -ferrate( III) sesq u ihyd rates, K3[M( 02C6H4 )3]. 1 . 5H20, M=chromium, iron," J. Am. Chem. Soc., Mar. 1976, 98(7), 1767-1774. cited by applicant.
Saito et al. "Dpph radical-scavenging reaction of protocatechuic acid: differnce in reactivity between acids and their esters," Hely Chim Acta, 2006, pp. 1395-1407, vol. 89.
Sever et al, "Visible absorption spectra of metal-catecholate and metal-tironate complexes," Dalton Trans., pp. 1061-1072, 2004.
SIGMA-ALDRICH Tris(hydroxymethyl)aminomethane, 2015.
Sommer, "Titanium (IV) complexes with ligands having oxygen donor atoms in aqueous solutions," Zeitschrift fur Anorganische and Aligemeine Chemie, Mar. 1963, pp. 191-197, vol. 321, issue 3-4.
Steenken, "One-electron redox potentials of phenols. Hydroxy- and aminophenols and related compounds of biological interest," J. Phys. Chem., Sep. 1982, 86(18), 3661-3667.
Torres-Gomez, "Energy Storage in Hybrid Organic-Inorganic Materials Hexacyanoferrate-Doped Polypyrrole as Cathode in Reversible Lithium Cells," J. of the Electrochemical Society, 2000, 147(7), 2513-2516.
Trant, "Solubility of Sodium Ferrocyanide and Potassium Ferrocyanide in Solutions of NaOH and KOH Mixtures at 25.degree. C," University of Rochester, The David T. Kearns Center, Xerox Undergraduate Research Fellows Program, Jul. 28, 2011, 1 page.
Vercillo, "Solubility of Sodium Ferrocyanide in Sodium Hydroxide and Potassium Ferrocyanide in Potassium Hydroxide," University of Rochester, The David T. Kearns Center, Xerox Undergraduate Research Fellows Program, Jul. 28, 2011, 1 page.
Wang, "Determination of iron, titanium, osmium, and aluminum with tiron by reversephase high performance liquid chromatography/electrochemistry," Microchem. J., Jun. 1991, 43(3), 191-197.

(56) References Cited

OTHER PUBLICATIONS

Weber, "Redox flow batteries: a review," Journal of Applied Electrochemistry, Oct. 2011, 41(10), 1137-1164.
Murakami et al., "The Chelating Behavior of Catechol-4-sulfonate with Iron(III) Ion," Bulletin of the Chemical Society of Japan, 1963, pp. 1408-1411; vol. 36.
Westervelt, "A Study of the Calcium Complex of the Potassium Salt of Catechol-4-Sulfonate in Aqueous, Alkalino Media," Jan. 1981, Doctoral Dissertation, retrieved from https://smartech.gatech.edu/bitstream/handle/1853/5723/westervelt-iii_hh.pdf.
W. Maison, et al., "Effect of Calcination Temperature on Phase Transformation and Particle size of Barium Titanate Fine Powders Synthesized by the Catecholate Process," ScienceAsia, 2001, pp. 239-243, 27.
Ahn et al., "A Study of Benzene 1,2,4-Trisphosphate Derivatives as Inositol 1,4,5-Trisphosphate 3-Kinase Inhibitors," Bull. Korean Chem. Soc., 2002, pp. 515-517, vol. 23., No. 3.
Bosch et al., "Novel Catalysis of Hydroquinone Autoxidation with Nitrogen Oxides," J. Org. Chem., 1994, pp. 2529-2536, 59.
Lang et al., "Studies on the Biosynthesis of Bovilactone-4,4 and Related Fungal Meroterpenoids," Eur. J. Org. Chem., 2008, pp. 3544-3551.
Lang et al., "Studies on the Structure and Biosynthesis of Tridentoquinone and Related Meroterpenoids from the Mushroom Suillus tridentinus (Boletales)," Eur. J. Org. Chem., 2008, pp. 816-825.
Mcomie et al. "The Thiele-Winter Acetoxylation of Quinones," Organic Reactions, 1972, pp. 199-277, 19, John Wiley and Sons, Inc., New York.
Spyroudis, "Hydroxyquinones: Synthesis and Reactivity," Molecules, 2000, pp. 1291-1330, 5.
Ali et al., "Synthesis and Processing Characteristics of $Ba_{0.65}Sr_{0.35}TiO_3$ Powders from Catecholate Precursors," J Am Ceram Soc, 1993, pp. 2321-2326, vol. 76, No. 9.
Devi et al., "pH-metric investigation on Mixed-Ligand Complexes of Ca(II), Mg(II) and Zn(II) with L-Dopa and 1,10 Phenantroline in Propylene glycol-Water Mixtures," RRJC, Oct.-Dec. 2012, vol. 1, Issue 1, pp. 13-22.
Xu, "Mechanics of metal-catecholate complexes: The roles of coordination state and metal types," Scientific Reports, Oct. 10, 2013, 3:2914, pp. 1-7.
Soloveichik, "Flow Batteries: Current Status and Trends," 2015, Chem. Rev., 115 (20), pp. 11533-11558.
Davies, "Electroceramics from Source Materials via Molecular Intermediates: $BaTIO_3$ from $TIO_2$ via $[TI(catecholate)_3]^{2-}$," May 1990, J. Am. Ceram. Soc., Aug. 1990, 73(5), 1429-30.
Vliet et al., "Hydroxyhydroquinone Triacetate," Organic Synthesys, 1941, Coll vol. 1, p. 317 (1941), vol. 4, p. 35 (1925) 3 pages.
International Search Report and Written Opinion dated Jan. 19, 2017 from International Application No. PCT/US16/58433.
International Search Report and Written Opinion dated Feb. 17, 2017 from International Application No. PCT/US16/65159.
Ahluwalia et al., Intermediates for Organic Synthesis, Chapter 1, Phenols, Sections 1.21 and 1.23, (2003), I.K. International Pvt. Ltd.
Abdulghani et al., "Preparation and Characterization of Di-, Tri-, and Tetranuclear Schiff Base Complexes Derived from Diamines and 3,4-Dihydroxybenzaldehyde," Hindawi Publishing Corp, Bioinorganic Chemistry and Applications, 2013, pp. 1-14.
IUPAC Compendium of Chemical Terminology, "coordinatively unsaturated complex," 1997, http://old.iupac.org/goldbook/C01334.pdf.
Mansoor, "Mixed Metal Complexes of Copper (II), Nickel (II) and Zinc (II) Involving Dopa and Dopamine," International Journal of ChemTech Research, Jan.-Mar. 2010, vol. 2, No. 1, pp. 640-645.
International Search Report and Written Opinion from PCT/US17/14764, dated Apr. 20, 2017.
International Search Report and Written Opinion from PCT/US16/69190, dated May 3, 2017.
International Search Report and Written Opinion from PCT/US2017/022203, dated Jun. 6, 2017.
Wang et al., "Issues in Freeze Drying of Aqueous Solutions," Chinese Journal of Chemical Engineering, 2012, 20(3), pp. 551-559.
International Search Report and Written Opinion from PCT/US17/43393, dated Oct. 5, 2017, 7 pages.

\* cited by examiner

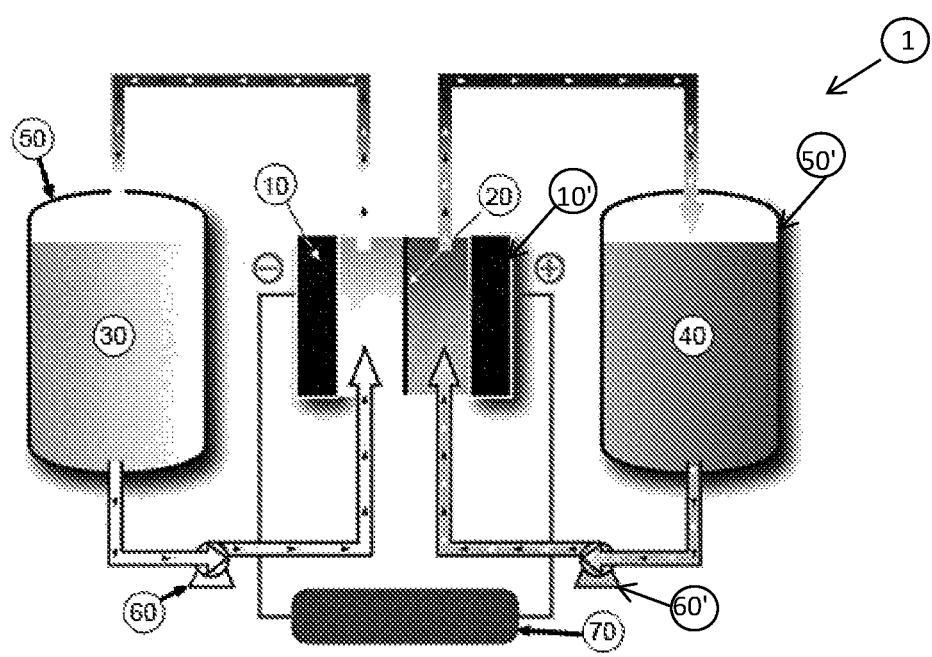

COORDINATION COMPOUNDS HAVING REDOX NON-INNOCENT LIGANDS AND FLOW BATTERIES CONTAINING THE SAME

CROSS-REFERENCE TO RELATED APPLICATIONS

Not applicable.

STATEMENT REGARDING FEDERALLY SPONSORED RESEARCH OR DEVELOPMENT

Not applicable.

FIELD

The present disclosure generally relates to energy storage and, more specifically, to flow batteries and other electrochemical systems containing coordination compounds as an active material within an electrolyte solution.

BACKGROUND

Electrochemical energy storage systems, such as batteries, supercapacitors and the like, have been widely proposed for large-scale energy storage applications. Various battery designs, including flow batteries, have been considered for this purpose. Compared to other types of electrochemical energy storage systems, flow batteries can be advantageous, particularly for large-scale applications, due to their ability to decouple the parameters of power density and energy density from one another.

Flow batteries generally include negative and positive active materials in corresponding electrolyte solutions, which are flowed separately across opposing sides of a membrane or separator in an electrochemical cell containing negative and positive electrodes. The flow battery is charged or discharged through electrochemical reactions of the active materials that occur inside the two half-cells. As used herein, the terms "active material," "electroactive material," "redox-active material" or variants thereof will synonymously refer to materials that undergo a change in oxidation state during operation of a flow battery or like electrochemical energy storage system (i.e., during charging or discharging). Although flow batteries hold significant promise for large-scale energy storage applications, they have often been plagued by sub-optimal energy storage performance (e.g., round trip energy efficiency) and limited cycle life, among other factors. Despite significant investigational efforts, no commercially viable flow battery technologies have yet been developed.

Metal-based active materials can often be desirable for use in flow batteries and other electrochemical energy storage systems. Although non-ligated metal ions (e.g., dissolved salts of a redox-active metal) can be used as an active material, it can often be more desirable to utilize coordination compounds for this purpose. As used herein, the terms "coordination complex, "coordination compound," and "metal-ligand complex" will synonymously refer to a compound having at least one covalent bond formed between a metal center and a donor ligand. The metal center can cycle between an oxidized form and a reduced form in an electrolyte solution, where the oxidized and reduced forms represent states of full charge or full discharge depending upon the particular half-cell in which the coordination compound is present. Because the oxidation-reduction cycle of many coordination compounds involves the transfer of only one electron at the metal center (i.e., a change in metal oxidation state of +1 or −1), the amount of charge that can be stored is frequently limiting, particularly for large-scale applications. That is, the ratio of transferred electrons per unit of coordination compound is low on a molar basis, typically a 1:1 ratio. Since solubility in an electrolyte solution is frequently a limiting parameter for coordination compounds and other metal-based active materials, there can be minimal opportunities to increase the energy density of a given flow battery configuration by altering the active material's concentration. Even when coordination compounds are used near their saturation concentration in an electrolyte solution, the energy density can still remain undesirably poor due to the low ratio of electrons transferred per unit of active material on a molar basis. Further, operating near an active material's saturation concentration can be precarious due to precipitation concerns. Not only can precipitation decrease the energy density of flow batteries by lowering the amount of available active material, but precipitation can also be problematic due to potential occlusion of circulation pathways and damage to other cell components.

In view of the foregoing, active materials for promoting enhanced energy density values in flow batteries would be highly desirable in the art. The present disclosure satisfies the foregoing need and provides related advantages as well.

SUMMARY

In some embodiments, the present disclosure provides flow batteries having a first half-cell containing a first electrolyte solution therein, where the first electrolyte solution contains a coordination compound having at least one redox non-innocent ligand coordinated to a metal center.

In other various embodiments, the present disclosure provides compositions containing a coordination compound having at least one redox non-innocent ligand coordinated to a metal center. The at least one redox non-innocent ligand contains a substituted catecholate or a salt thereof bearing a quinone functional group.

The foregoing has outlined rather broadly the features of the present disclosure in order that the detailed description that follows can be better understood. Additional features and advantages of the disclosure will be described hereinafter. These and other advantages and features will become more apparent from the following description.

BRIEF DESCRIPTION OF THE DRAWINGS

For a more complete understanding of the present disclosure, and the advantages thereof, reference is now made to the following descriptions to be taken in conjunction with the accompanying drawings describing specific embodiments of the disclosure, wherein:

FIG. 1 depicts a schematic of an illustrative flow battery.

DETAILED DESCRIPTION

The present disclosure is directed, in part, to flow batteries and compositions containing coordination compounds as active materials, where the coordination compounds contain at least one redox non-innocent ligand. The present disclosure is also directed, in part, to particular compositions containing a coordination compound having at least one redox non-innocent ligand coordinated to a metal center, where the at least one redox non-innocent ligand bears a quinone functional group.

The present disclosure may be understood more readily by reference to the following description taken in connection with the accompanying figures and examples, all of which form a part of this disclosure. It is to be understood that this disclosure is not limited to the specific products, methods, conditions or parameters described and/or shown herein. Further, the terminology used herein is for purposes of describing particular embodiments by way of example only and is not intended to be limiting unless otherwise specified. Similarly, unless specifically stated otherwise, any description herein directed to a composition is intended to refer to both solid and liquid versions of the composition, including solutions and electrolytes containing the composition, and electrochemical cells, flow batteries, and other energy storage systems containing such solutions and electrolytes. Further, it is to be recognized that where the disclosure herein describes an electrochemical cell, flow battery, or other energy storage system, it is to be appreciated that methods for operating the electrochemical cell, flow battery, or other energy storage system are also implicitly described.

It is also to be appreciated that certain features of the present disclosure may be described herein in the context of separate embodiments for clarity purposes, but may also be provided in combination with one another in a single embodiment. That is, unless obviously incompatible or specifically excluded, each individual embodiment is deemed to be combinable with any other embodiment(s) and the combination is considered to represent another distinct embodiment. Conversely, various features of the present disclosure that are described in the context of a single embodiment for brevity's sake may also be provided separately or in any sub-combination. Finally, while a particular embodiment may be described as part of a series of steps or part of a more general structure, each step or sub-structure may also be considered an independent embodiment in itself.

Unless stated otherwise, it is to be understood that each individual element in a list and every combination of individual elements in that list is to be interpreted as a distinct embodiment. For example, a list of embodiments presented as "A, B, or C" is to be interpreted as including the embodiments "A," "B," "C," "A or B," "A or C," "B or C," or "A, B, or C."

In the present disclosure, the singular forms of the articles "a," "an," and "the" also include the corresponding plural references, and reference to a particular numerical value includes at least that particular value, unless the context clearly indicates otherwise. Thus, for example, reference to "a material" is a reference to at least one of such materials and equivalents thereof.

In general, use of the term "about" indicates approximations that can vary depending on the desired properties sought to be obtained by the disclosed subject matter and is to be interpreted in a context-dependent manner based on functionality. Accordingly, one having ordinary skill in the art will be able to interpret a degree of variance on a case-by-case basis. In some instances, the number of significant figures used when expressing a particular value may be a representative technique of determining the variance permitted by the term "about." In other cases, the gradations in a series of values may be used to determine the range of variance permitted by the term "about." Further, all ranges in the present disclosure are inclusive and combinable, and references to values stated in ranges include every value within that range.

As discussed above, energy storage systems that can be operated on a large scale while maintaining high operating efficiencies can be extremely desirable. Flow batteries have generated significant interest in this regard, but there remains considerable room for improving their operating characteristics. In particular, the low ratio of electrons transferred per unit of active material on a molar basis can frequently be limiting when coordination compounds are utilized in flow batteries. Exemplary description of illustrative flow batteries, their use, and operating characteristics is provided hereinbelow.

The present inventor recognized that the energy density of flow batteries and other electrochemical systems could be improved by increasing the ratio of electrons transferred per unit of active material on a molar basis during an oxidation-reduction cycle. For many coordination compounds, this ratio is fixed at a value of one and is based upon oxidation and reduction of the metal center within the coordination compound. Vanadium- and zinc-based active materials are notable exceptions, but they have notable limitations. The present inventor recognized that alternative coordination compounds containing at least one ligand that is also capable of undergoing reversible oxidation and reduction within the working electrochemical window of an electrolyte solution could result in significantly increased quantities of transferred electrons on a molar basis and improved energy density values. As used herein, the term "working electrochemical window" will refer to the range of electrical potentials over which the solvent of an electrolyte solution is neither oxidized nor reduced and remains stable. Accordingly, in the embodiments of the present disclosure, both the metal center and one or more ligands of a coordination compound can undergo reversible oxidation and reduction within the working electrochemical window of an electrolyte solution to increase the number of electrons transferred on a molar basis.

As used herein, the term "redox non-innocent ligand" will refer to a donor molecule in a coordination compound that can undergo reversible oxidation and reduction, such as within the working electrochemical window of an electrolyte solution in which the coordination compound is disposed. The oxidation and reduction potentials of the coordination compound's metal center can likewise reside within the working electrochemical window of the electrolyte solution. Hence, coordination compounds containing a redox non-innocent ligand can acquire multiple oxidation states that result in an ability to transfer multiple electrons on a molar basis.

In coordination compounds containing at least one redox non-innocent ligand, the overall oxidation state of the metal center is no longer clear. That is, the change in oxidation state of such coordination compounds can be metal-based, ligand-based, or a combination thereof. As a result, the number of electrons that are transferred in proceeding from a fully oxidized state to a fully reduced state, or vice versa, can be higher than in coordination compounds in which the ligands are not redox active. For purposes of this disclosure, ligands that are non-redox active will be considered to be "innocent."

Accordingly, the present inventor discovered that the energy density of existing flow battery configurations can be readily increased by utilizing a coordination compound containing at least one redox non-innocent ligand within at least one of the flow battery's half-cells. Specifically, by substituting an electrolyte solution containing a "one-electron" coordination compound (i.e., a coordination compound with only innocent ligands) as an active material with an electrolyte solution containing a "multi-electron" coordination compound (i.e., a coordination compound containing at least one redox non-innocent ligand) as an active material, improved energy density values can be realized. Since such improvements can be realized by merely replacing one coordination compound with another, no significant engineering changes to the flow battery configuration are generally needed. Although the composition of the electrolyte solution (e.g., pH, buffers, surfactants, and/or the like) may need to be altered in view of possible differences in solubility and/or chemistry of the coordination compound containing the at least one redox non-innocent ligand, such alterations are considered to lie within the purview of one having ordinary skill in the art.

Not only do coordination compounds containing at least one redox non-innocent ligand offer increased energy density values in flow batteries and other electrochemical systems, but they also offer further operational advantages as well. Because such coordination compounds can transfer multiple electrons during an oxidation-reduction cycle, lower-concentration electrolyte solutions can be utilized while still preserving increased energy density values. That is, the drop in the amount of transferred electrons upon decreasing the coordination compound's concentration can be more than offset by the increased number of electrons transferred per unit of active material on a molar basis. At the very least, lower-concentration electrolyte solutions can be desirable from a cost of materials standpoint. Further, by utilizing a coordination compound at a concentration more removed from that of its saturation concentration, there can be a significantly decreased risk of unwanted precipitation within the electrolyte solution. Hence, the coordination compounds described herein can help avert damaging precipitation within flow batteries and their various components. Alternately, because they can be used effectively at lower concentrations than can "one-electron" coordination compounds, the coordination compounds described herein can contain ligands (innocent and/or redox non-innocent ligands) that inherently lead to lower solubility values but still allow suitable energy density values to be maintained. Thus, coordination compounds containing at least one redox non-innocent ligand can allow a much greater breadth in the choice of ligand structure to be realized than would otherwise be possible.

Depending on the extent to which one wishes to increase the quantity of electrons transferred per unit of active material on a molar basis, the number of redox non-innocent ligands present within the coordination compound can be varied to accordingly. If one wants to increase the number of transferred electrons only minimally, a coordination compound containing only one redox non-innocent ligand can be utilized. Coordination compounds having more than one redox non-innocent ligand can be used to increase the number of transferred electrons further. Any number of redox non-innocent ligands can be present in the coordination compounds of the present disclosure up to the metal center's maximum number of open coordination sites. Any coordination sites that are not occupied by redox non-innocent ligands can be occupied by innocent ligands. Hence, the use of redox non-innocent ligands allows further diversification in the coordination compound chemistry to be realized.

Although the reversibly oxidizable and reducible functional groups of a redox non-innocent ligand can directly complex the metal center in a coordination compound, it can be more desirable that the functional groups producing the redox non-innocent behavior do not complex the metal center directly. Otherwise, the bond connecting the redox non-innocent ligand to the metal center may break upon the functional groups undergoing a change in oxidation state. Instead, the redox-active functional groups within the redox non-innocent ligand can be separated from innocent functional groups that are coordinated to the metal center.

As discussed above, redox non-innocent ligands contain reversibly oxidizable and reducible functional groups that allow their coordination compounds to transfer multiple electrons during an oxidation-reduction cycle. Any number of electrons can be transferred upon oxidation or reduction of these functional groups depending upon the change in oxidation state. However, functional groups that facilitate transfer of two electrons can be present in common embodiments. Such functional groups will be referred to herein as "two-electron functional groups," particularly desirable examples of which are discussed hereinafter.

Quinones can be particularly desirable two-electron functional groups for inclusion in redox non-innocent ligands. Quinone-based ligands can be particularly desirable redox non-innocent ligands for a number of reasons. First, quinone functional groups are readily oxidizable and reducible at electrical potentials comparable to those of many transition metal centers of interest, and the redox process is highly reversible with facile kinetics. Further, the oxidation/reduction potentials of quinone functional groups are generally compatible with the working electrochemical window of many common electrolyte solutions of interest, including aqueous solutions. Second, quinone functional groups can also be particularly advantageous when included in catecholate ligands, a class of ligands that can be particularly desirable for forming flow battery active materials, especially the active material present in the negative half-cell of a flow battery. Quinone functional groups can be similarly advantageous in compounds containing other chelating functional groups, such as those containing nitrogen functional groups and/or sulfur functional groups and/or a mixture of these functional groups with oxygen functional groups. Although coordination compounds containing catecholate ligands can be particularly desirable active materials for flow batteries, the catechol functional group can sometimes be susceptible toward oxidative degradation when not bound to a metal center, thereby potentially damaging a flow battery and/or decreasing its energy storage performance. Advantageously, electron-withdrawing quinone functional groups can at least partially stabilize catechol groups, promote complexation, and decrease their propensity toward degradation. Hence, quinone functional groups can serve a dual role of stabilizing catecholate ligands and promoting the transfer of multiple electrons during an oxidation-reduction cycle. Inclusion of quinone functional groups within a catecholate ligand can also serve to alter the solubility profile of the catecholate ligand and coordination compounds formed therefrom.

Quinone functional groups (both 1,2-quinones and 1,4-quinones) can be especially effective in stabilizing catecholate ligands when the quinone functional group is fused to the aromatic ring bearing the catechol functional group or is within the aromatic ring bearing the catechol functional group. In this regard, a number of catecholate ligands bearing a fused 1,4-quinone functional group (i.e., naphthoquinones and anthraquinones) are accessible synthetically and/or are commercially available at reasonable cost. Accordingly, utilizing a catecholate ligand bearing a quinone functional group as a redox non-innocent ligand can facilitate the advantages discussed hereinabove.

In various embodiments, the present disclosure describes compositions and flow batteries containing an active material that is capable of transferring multiple electrons in a single oxidation-reduction cycle. More specifically, the active material can be a coordination compound having at least one redox non-innocent ligand coordinated to a metal center. In more specific embodiments, the at least one redox non-innocent ligand can be a substituted catecholate or a salt thereof bearing a quinone functional group. As used herein, the term "catechol" will refer to a compound having an aromatic ring bearing hydroxyl groups on adjacent carbon atoms (i.e., 1,2-hydroxyl groups). The term "catecholate" will refer to a catechol compound that is bound to a metal center via a metal-ligand bond.

Accordingly, in various embodiments, flow batteries of the present disclosure can include a first half-cell having a first electrolyte solution therein. The first electrolyte solution contains a coordination compound having at least one redox non-innocent ligand coordinated to a metal center. In some embodiments, the metal center can be a transition metal. Further disclosure regarding suitable redox non-innocent ligands and transition metal complexes thereof follows hereinbelow. Exemplary description of flow batteries and their operating characteristics are also discussed in more detail hereinbelow.

In more specific embodiments, the at least one redox non-innocent ligand can bear a quinone functional group. As discussed above, quinone functional groups can be advantageous from the standpoint of being reversibly oxidizible and reducible under mild conditions in common solvents, including aqueous solutions, which can be desirable in the context of flow batteries. Both 1,2- and 1,4-quinones can be used in the embodiments of the present disclosure. However, in more particular embodiments, the at least one redox non-innocent ligand can contain a 1,4-quinone functional group. 1,4-quinones are also particularly desirable since they are not believed to coordinate to a metal center. Functional groups other than quinones that can be present in a redox non-innocent ligand include, for example, nitroso groups, thiolate functional groups, dithiolene functional groups, imine functional groups, aldehyde functional groups, carboxylic acid functional groups, carboxylic ester functional groups, and the like.

As discussed above, quinone functional groups can also help stabilize electron-rich functional groups, such as catechols. Accordingly, in some embodiments, the at least one redox non-innocent ligand can include a substituted catechol or a salt thereof bearing a quinone functional group. Illustrative examples are provided hereinbelow.

Redox non-innocent ligands based upon a substituted catechol bearing a quinone functional group are not believed to be particularly limited in structure. The quinone functional group can be part of the aromatic ring bearing the catechol group, fused to the aromatic ring bearing the catechol group, or tethered via a linker to the aromatic ring bearing the catechol group. Illustrative examples are provided hereinbelow.

In more particular embodiments, the redox non-innocent ligand can be a naphthoquinone or an anthraquinone in which the quinone functional group is directly fused to the aromatic ring bearing the catechol functional group. In some embodiments, the at least one redox non-innocent ligand can be a naphthoquinone or an anthraquinone having one of the following structures:

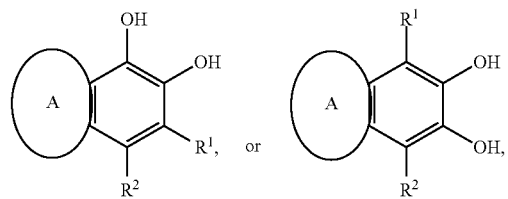

wherein $R^1$ and $R^2$ are independently H, $OR^3$ ($R^3$=H or alkyl), alkyl, heteroatom-substituted alkyl, halide, $CO_2R^3$ or $SO_3R^3$, and A is a quinone-containing ring fused to the aromatic ring bearing the catechol group. Specifically, A can have one of the following structures:

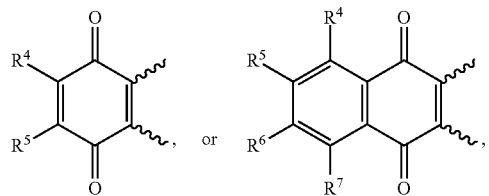

wherein $R^4$, $R^5$, $R^6$ and $R^7$ are independently H, $OR^3$ ($R^3$=H or alkyl), alkyl, heteroatom-substituted alkyl, halide, $CO_2R^3$, or $SO_3R^3$.

In more particular embodiments, the at least one redox non-innocent ligand can be a naphthoquinone or anthraquinone having a structure selected from among the following:

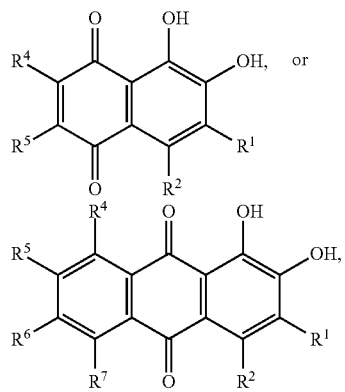

wherein $R^1$ and $R^2$ are independently H, OH, or $SO_3H$, and $R^4$-$R^7$ are independently H, $OR^3$, $CO_2R^3$ or alkyl.

In still more specific embodiments, suitable naphthoquinones and anthraquinones that can constitute the at least one redox non-innocent ligand can be selected from among the following structures:

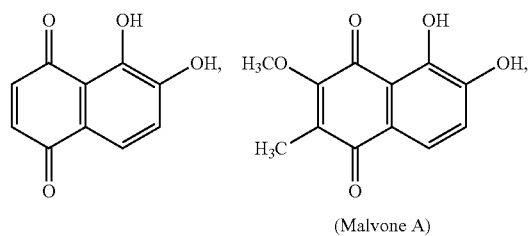

(Malvone A)

-continued

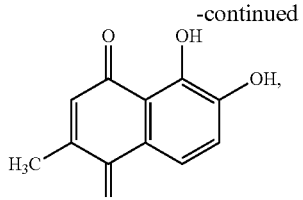
(6-hydroxyplumbagin)

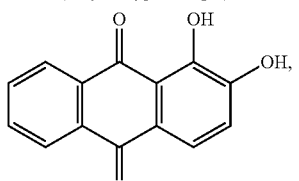
(Alizarin)

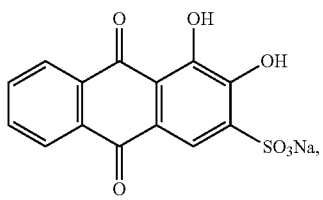
(Alizarin-S)

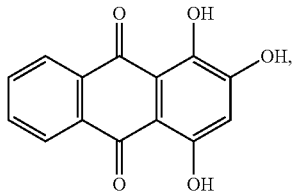
(Purpurin)

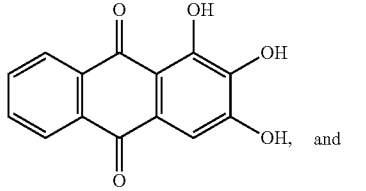
and

In other various embodiments, the redox non-innocent ligand can bear the quinone functional group in the same ring as the catechol functional group. Illustrative compounds in this regard can include, for example,

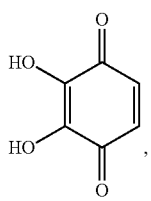 , 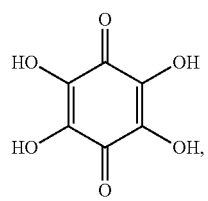 ,

-continued

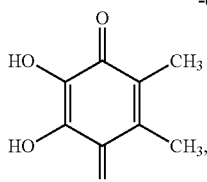 , and 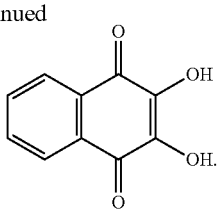
(Isonaphthazin)

In still more specific embodiments, the at least one redox non-innocent ligand can be selected from among the following compounds:

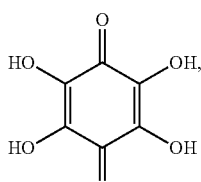 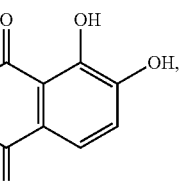

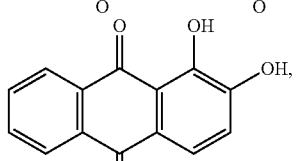

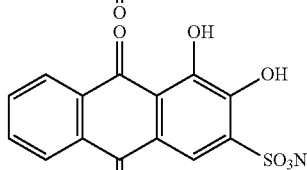

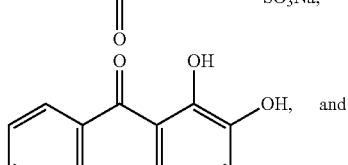 and

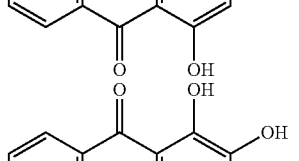

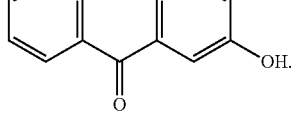

Due to their variable oxidation states, transition metals can be highly desirable for use within the active material of a flow battery. Cycling between the accessible oxidation states can result in the conversion of chemical energy into electrical energy. Lanthanide elements can be used similarly in this regard. In general, any transition metal or lanthanide metal can be present as the metal center in the coordination compounds of the present disclosure. In more specific embodiments, the metal center can be a transition metal selected from among Al, Cr, Ti and Fe. For purposes of the present disclosure, Al is to be considered a transition metal. In more specific embodiments, the transition metal can be Ti. Other suitable transition and main group metals that can be present in the coordination compounds of the present disclosure include, for example, Ca, Ce, Co, Cu, Mg, Mn, Mo, Ni, Pd, Pt, Ru, Sr, Sn, V, Zn, Zr, and any combination thereof. In various embodiments, the coordination compounds can include a transition metal in a non-zero oxidation state when the transition metal is in both its oxidized and reduced forms. Cr, Fe, Mn, Ti and V can be particularly desirable in this regard.

In various embodiments, coordination compounds of the present disclosure can contain at least one redox non-innocent ligand coordinated to the metal center. In some embodiments, one redox non-innocent ligand can be present in the coordination compounds. In other various embodiments, two redox non-innocent ligands, or three redox non-innocent ligands, or four redox non-innocent ligands, or five redox non-innocent ligands, or six redox non-innocent ligands can be present in the coordination compounds. The maximum number of redox non-innocent ligands that may be present can be dictated by the number of available coordination sites at the metal center. In some embodiments, the redox non-innocent ligand can form a chelate with the metal center, and in such embodiments, one, two, or three chelating redox non-innocent ligands can usually be present in the coordination compounds. Quinone-based substituted catecholate ligands represent an illustrative class of chelating redox non-innocent ligands. When multiple redox non-innocent ligands are present, the redox non-innocent ligands can be the same or different, and in some embodiments, a mixture of chelating redox non-innocent ligands and non-chelating redox non-innocent ligands can be present. Any coordination sites not occupied by the at least one redox non-innocent ligand can be filled with innocent ligands, illustrative examples of which are discussed below. In alternative embodiments, a redox non-innocent ligand can also be bound to a metal center in a monodentate fashion.

In more specific embodiments, coordination compounds of the present disclosure can have a formula of

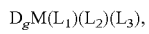

wherein M is a transition metal; D is ammonium, tetraalkylammonium ($C_1$-$C_4$ alkyl), or an alkali metal ion (e.g., $Li^+$, $Na^+$ or $K^+$); g ranges between 0 and 6; and $L_1$, $L_2$ and $L_3$ are ligands and at least one of $L_1$, $L_2$ and $L_3$ is the redox non-innocent ligand. In more specific embodiments, the at least one redox non-innocent ligand can be a substituted catecholate bearing a quinone functional group, as discussed in more detail above. In some embodiments, each of $L_1$, $L_2$ and $L_3$ can be a substituted catecholate bearing a quinone functional group. In other embodiments, one or two of $L_1$, $L_2$ and $L_3$ can be a substituted catecholate bearing a quinone functional group, and any of $L_1$, $L_2$ and $L_3$ that are not the substituted catecholate can be an innocent ligand. In still more specific embodiments, one or two of $L_1$, $L_2$ and $L_3$ can be a substituted catecholate bearing a quinone functional group, and at least one of $L_1$, $L_2$ and $L_3$ can be an innocent catecholate or substituted catecholate.

In some embodiments, innocent ligands that can be included in the coordination complexes of the present disclosure include, for example, an unsubstituted catecholate, a substituted catecholate, ascorbate, citrate, glycolate, a polyol, gluconate, hydroxyalkanoate, acetate, formate, benzoate, malate, maleate, phthalate, sarcosinate, salicylate, oxalate, urea, polyamine, aminophenolate, acetylacetonate, and lactate. Where chemically feasible, it is to be recognized that the ligands defined in the foregoing lists can be optionally substituted with at least one group selected from among $C_{1-6}$ alkoxy, $C_{1-6}$ alkyl, $C_{1-6}$ alkenyl, $C_{1-6}$ alkynyl, 5- or 6-membered aryl or heteroaryl groups, a boronic acid or a derivative thereof, a carboxylic acid or a derivative thereof, cyano, halide, hydroxyl, nitro, sulfonate, a sulfonic acid or a derivative thereof, a phosphonate, a phosphonic acid or a derivative thereof, or a glycol, such as polyethylene glycol. Alkanoate includes any of the alpha, beta, and gamma forms of these ligands. Polyamines include, but are not limited to, ethylenediamine, ethylenediamine tetraacetic acid (EDTA), and diethylenetriamine pentaacetic acid (DTPA).

Examples of monodentate innocent ligands that can be present in the coordination compounds of the present disclosure include, for example, carbonyl or carbon monoxide, nitride, oxo, hydroxo, water, sulfide, thiols, pyridine, pyrazine, and the like. Examples of innocent bidentate ligands that can be present in the coordination compounds of the present disclosure include, for example, bipyridine, bipyrazine, ethylenediamine, diols (including ethylene glycol), and the like. Examples of tridentate innocent ligands that can be present in the coordination compounds of the present disclosure include, for example, terpyridine, diethylenetriamine, triazacyclononane, tris(hydroxymethyl)aminomethane, and the like.

Accordingly, the present disclosure describes in some embodiments compositions that include a coordination compound having at least one redox non-innocent ligand coordinated to a metal center, where the at least one redox non-innocent ligand is a substituted catecholate or a salt thereof bearing a quinone functional group. Suitable redox non-innocent ligands and metal centers are specified in more detail above.

In some embodiments, the electrolyte solution used within the flow batteries of the present disclosure can be an aqueous solution. Compositions of the present disclosure can similarly include an aqueous solution in which the coordination compound is disposed. As used herein, the term "aqueous solution" will refer to a homogeneous liquid phase with water as a predominant solvent in which a component of interest (e.g., a coordination compound or other active material) is at least partially solubilized, ideally fully solubilized. This definition encompasses both solutions in water and solutions containing a water-miscible organic solvent as a minority component of an aqueous phase.

Illustrative water-miscible organic solvents that can be present in the aqueous solution include, for example, alcohols and glycols, optionally in the presence of one or more surfactants or other components discussed below. In more specific embodiments, the aqueous solution can contain at least about 98% water by weight. In other more specific embodiments, the aqueous solution can contain at least about 55% water by weight, or at least about 60% water by weight, or at least about 65% water by weight, or at least about 70% water by weight, or at least about 75% water by weight, or at least about 80% water by weight, or at least about 85% water by weight, or at least about 90% water by weight, or at least about 95% water by weight. In some embodiments, the aqueous solution can be free of water-miscible organic solvents and consist of water alone as a solvent.

In further embodiments, the aqueous solution can include a viscosity modifier, a wetting agent, or any combination thereof. Suitable viscosity modifiers can include, for example, corn starch, corn syrup, gelatin, glycerol, guar gum, pectin, and the like. Other suitable examples will be familiar to one having ordinary skill in the art. Suitable wetting agents can include, for example, various non-ionic surfactants and/or detergents. In some or other embodiments, the aqueous solution can further include a glycol or a polyol. Suitable glycols can include, for example, ethylene glycol, diethylene glycol, and polyethylene glycol. Suitable polyols can include, for example, glycerol, mannitol, sorbitol, pentaerythritol, and tris(hydroxymethyl)aminomethane. Inclusion of any of these components in the aqueous solution can help promote dissolution of the coordination compound and/or reduce viscosity of the aqueous solution for conveyance through a flow battery, for example.

In illustrative embodiments, the electrolyte solution of a flow battery containing the coordination compounds disclosed above can be an aqueous solution that is maintained at an alkaline pH. As used herein, the term "alkaline pH" will refer to any pH value between 7 and 14. In some embodiments, one or more buffers can be present to help maintain the pH at an alkaline pH value. In more specific embodiments, the electrolyte solution can be maintained at a pH of about 9 to about 12. A pH residing within a range of about 9 to about 12 can be particularly desirable for maintaining a substituted catecholate ligand in a deprotonated state and complexed to the metal center of a coordination compound of interest. Other illustrative alkaline pH ranges that can be maintained in the electrolyte solution include, for example, about 7 to about 7.5, or about 7.5 to about 8, or about 8 to about 8.5, or about 8.5 to about 9, or about 9.5 to about 10, or about 10 to about 10.5, or about 10.5 to about 11, or about 11 to about 11.5, or about 11.5 to about 12, or about 12 to about 12.5, or about 12.5 to about 13, or about 13 to about 13.5, or about 13.5 to about 14. Illustrative buffers that can be suitable include, but are not limited to, salts of phosphates, borates, carbonates, silicates, tris(hydroxymethyl)aminomethane (TRIS), 4-(2-hydroxyethyl)-1-piperazineethanesulfonic acid (HEPES), piperazine-N,N'-bis(ethanesulfonic acid) (PIPES), or any combination thereof.

In alternative embodiments in which the redox non-innocent ligand is not a substituted catecholate, non-alkaline pH values can be present in the electrolyte solution. For example, in illustrative embodiments, the pH of the electrolyte solution can be acidic such as having a pH value ranging between 1 and about 3, or between about 2 and about 5, or between about 4 and about 6, or between about 5 and about 7.

In addition to a solvent and a coordination compound as an active material, the electrolyte solution can also include one or more mobile ions. In some embodiments, suitable mobile ions can include proton, hydronium, or hydroxide. In other various embodiments, mobile ions other than proton, hydronium, or hydroxide can be present, either alone or in combination with proton, hydronium or hydroxide, Such alternative mobile ions can include, for example, alkali metal or alkaline earth metal cations (e.g., $Li^+$, $Na^+$, $K^+$, $Mg^{2+}$, $Ca^{2+}$ and $Sr^{2+}$) and halides (e.g., $F^-$, $Cl^-$, or $Br^-$). Other suitable mobile ions can include, for example, ammonium and tetraalkylammonium ions, chalcogenides, phosphate, hydrogen phosphate, phosphonate, nitrate, sulfate, nitrite, sulfite, perchlorate, tetrafluoroborate, hexafluorophosphate, and any combination thereof. In some embodiments, less than about 50% of the mobile ions can constitute protons, hydronium, or hydroxide. In other various embodiments, less than about 40%, less than about 30%, less than about 20%, less than about 10%, less than about 5%, or less than about 2% of the mobile ions can constitute protons, hydronium, or hydroxide.

In various embodiments, a concentration of the coordination compound in the electrolyte solution can range between about 0.1 M and about 3 M. This concentration range represents the sum of the individual concentrations of the oxidized and reduced forms of the coordination compound. In more particular embodiments, the concentration of the coordination compound can range between about 0.5 M and about 3 M, or between 1 M and about 3 M, or between about 1.5 M and about 3 M, or between 1 M and about 2.5 M.

In still more specific embodiments, flow batteries of the present disclosure can further include a second half-cell having a second electrolyte solution therein, where the second electrolyte solution contains an iron hexacyanide complex. Iron hexacyanide complexes can be particularly desirable due to their facile electrode kinetics and reversible electrochemical behavior at oxidation-reduction potentials near the working electrochemical window of aqueous solutions. Hence, they can allow high open circuit potentials and cell efficiencies to be realized. In more specific embodiments, flow batteries of the present disclosure can include the first electrolyte solution in contact with a negative electrode of the flow battery and the second electrolyte solution in contact with the positive electrode of the flow battery.

Illustrative flow battery configurations that can incorporate the foregoing electrolyte solutions and coordination compounds will now be described in further detail. The flow batteries of the present disclosure are, in some embodiments, suited to sustained charge or discharge cycles of several hour durations. As such, they can be used to smooth energy supply/demand profiles and provide a mechanism for stabilizing intermittent power generation assets (e.g., from renewable energy sources such as solar and wind energy). It should be appreciated, then, that various embodiments of the present disclosure include energy storage applications where such long charge or discharge durations are desirable. For example, in non-limiting examples, the flow batteries of the present disclosure can be connected to an electrical grid to allow renewables integration, peak load shifting, grid firming, baseload power generation and consumption, energy arbitrage, transmission and distribution asset deferral, weak grid support, frequency regulation, or any combination thereof. When not connected to an electrical grid, the flow batteries of the present disclosure can be used as power sources for remote camps, forward operating bases, off-grid telecommunications, remote sensors, the like, and any combination thereof. Further, while the disclosure herein is generally directed to flow batteries, it is to be appreciated that other electrochemical energy storage media can incorporate the electrolyte solutions and coordination compounds described herein, specifically those utilizing stationary electrolyte solutions.

In some embodiments, flow batteries of the present disclosure can include: a first chamber containing a negative electrode contacting a first aqueous electrolyte solution; a second chamber containing a positive electrode contacting a second aqueous electrolyte solution, and a separator disposed between the first and second electrolytes solutions. The chambers provide separate reservoirs within the cell, through which the first and/or second electrolyte solutions circulate so as to contact the respective electrodes and the separator. Each chamber and its associated electrode and electrolyte solution define a corresponding half-cell. The separator provides several functions which include, for example, (1) serving as a barrier to mixing of the first and second electrolyte solutions, (2) electrically insulating to reduce or prevent short circuits between the positive and negative electrodes, and (3) to facilitate ion transport between the positive and negative electrolyte chambers, thereby balancing electron transport during charge and discharge cycles. The negative and positive electrodes provide a surface where electrochemical reactions can take place during charge and discharge cycles. During a charge or discharge cycle, electrolyte solutions can be transported from separate storage tanks through the corresponding chambers. In a charging cycle, electrical power can be applied to the cell such that the active material contained in the second electrolyte solution undergoes a one or more electron oxidation and the active material in the first electrolyte solution undergoes a one or more electron reduction. Similarly, in a discharge cycle the second active material is reduced and the first active material is oxidized to generate electrical power.

In more specific embodiments, illustrative flow batteries of the present disclosure can include: (a) a first aqueous electrolyte solution containing a first coordination compound; (b) a second aqueous electrolyte solution containing a second coordination compound; (c) a separator positioned between said first and second aqueous electrolyte solutions; and (d) mobile ion in the first and second aqueous electrolyte solutions. As described in more detail below, the separator can be an ionomer membrane, and it can have a thickness of less than 100 microns and have an associated net charge that is the same sign as that of the first and second coordination compounds.

FIG. 1 depicts a schematic of an illustrative flow battery. Unlike typical battery technologies (e.g., Li-ion, Ni-metal hydride, lead-acid, and the like), where active materials and other components are housed in a single assembly, flow batteries transport (e.g., via pumping) redox active energy storage materials from storage tanks through an electrochemical stack. This design feature decouples the electrical energy storage system power from the energy storage capacity, thereby allowing for considerable design flexibility and cost optimization.

As shown in FIG. 1, flow battery system 1 includes an electrochemical cell that features separator 20 (e.g., a membrane) that separates the two electrodes 10 and 10' of the electrochemical cell. Electrodes 10 and 10' are formed from a suitably conductive material, such as a metal, carbon, graphite, and the like. Tank 50 contains first active material 30, which is capable of being cycled between an oxidized state and a reduced state.

Pump 60 affects transport of first active material 30 from tank 50 to the electrochemical cell. The flow battery also suitably includes second tank 50' that contains second active material 40. Second active material 40 can be the same material as active material 30, or it can be different. Second pump 60' can affect transport of second active material 40 to the electrochemical cell. Pumps can also be used to affect transport of the active materials from the electrochemical cell back to tanks 50 and 50' (not shown in FIG. 1). Other methods of affecting fluid transport, such as siphons, for example, can also suitably transport first and second active materials 30 and 40 into and out of the electrochemical cell. Also shown in FIG. 1 is power source or load 70, which completes the circuit of the electrochemical cell and allows a user to collect or store electricity during its operation.

It should be understood that FIG. 1 depicts a specific, non-limiting embodiment of a flow battery. Accordingly, flow batteries consistent with the spirit of the present disclosure can differ in various aspects relative to the configuration of FIG. 1. As one example, a flow batter system can include one or more active materials that are solids, gases, and/or gases dissolved in liquids. Active materials can be stored in a tank, in a vessel open to the atmosphere, or simply vented to the atmosphere.

As used herein, the terms "separator" and "membrane" refer to an ionically conductive and electrically insulating material disposed between the positive and negative electrodes of an electrochemical cell. The separator can be a porous membrane in some embodiments and/or an ionomer membrane in other various embodiments. In some embodiments, the separator can be formed from an ionically conductive polymer.

Polymer membranes can be anion- or cation-conducting electrolytes. Where described as an "ionomer," the term refers to polymer membrane containing both electrically neutral repeating units and ionized repeating units, where the ionized repeating units are pendant and covalently bonded to the polymer backbone. In general, the fraction of ionized units can range from about 1 mole percent to about 90 mole percent. For example, in some embodiments, the content of ionized units is less than about 15 mole percent; and in other embodiments, the ionic content is higher, such as greater than about 80 mole percent. In still other embodiments, the ionic content is defined by an intermediate range, for example, in a range of about 15 to about 80 mole percent. Ionized repeating units in an ionomer can include anionic functional groups such as sulfonate, carboxylate, and the like. These functional groups can be charge balanced by, mono-, di-, or higher-valent cations, such as alkali or alkaline earth metals. Ionomers can also include polymer compositions containing attached or embedded quaternary ammonium, sulfonium, phosphazenium, and guanidinium residues or salts. Suitable examples will be familiar to one having ordinary skill in the art.

In some embodiments, polymers useful as a separator can include highly fluorinated or perfluorinated polymer backbones. Certain polymers useful in the present disclosure can include copolymers of tetrafluoroethylene and one or more fluorinated, acid-functional co-monomers, which are commercially available as NAFION™ perfluorinated polymer electrolytes from DuPont. Other useful perfluorinated polymers can include copolymers of tetrafluoroethylene and $FSO_2$—$CF_2CF_2CF_2CF_2$—O—CF=$CF_2$, FLEMION™ and SELEMION™.

Additionally, substantially non-fluorinated membranes that are modified with sulfonic acid groups (or cation exchanged sulfonate groups) can also be used. Such membranes can include those with substantially aromatic backbones such as, for example, polystyrene, polyphenylene, biphenyl sulfone (BPSH), or thermoplastics such as polyetherketones and polyethersulfones.

Battery-separator style porous membranes, can also be used as the separator. Because they contain no inherent ionic conduction capabilities, such membranes are typically impregnated with additives in order to function. These membranes typically contain a mixture of a polymer and inorganic filler, and open porosity. Suitable polymers can include, for example, high density polyethylene, polypropylene, polyvinylidene difluoride (PVDF), or polytetrafluoroethylene (PTFE). Suitable inorganic fillers can include silicon carbide matrix material, titanium dioxide, silicon dioxide, zinc phosphide, and ceria.

Separators can also be formed from polyesters, polyetherketones, polyvinyl chloride), vinyl polymers, and substituted vinyl polymers. These can be used alone or in combination with any previously described polymer.

Porous separators are non-conductive membranes which allow charge transfer between two electrodes via open channels filled with electrolyte. The permeability increases the probability of chemicals (e.g., active materials) passing through the separator from one electrode to another and causing cross-contamination and/or reduction in cell energy efficiency. The degree of this cross-contamination can depend on, among other features, the size (the effective diameter and channel length), and character (hydrophobicity/hydrophilicity) of the pores, the nature of the electrolyte, and the degree of wetting between the pores and the electrolyte.

The pore size distribution of a porous separator is generally sufficient to substantially prevent the crossover of active materials between the two electrolyte solutions. Suitable porous membranes can have an average pore size distribution of between about 0.001 mm and 20 micrometers, more typically between about 0.001 nm and 100 nm. The size distribution of the pores in the porous membrane can be substantial. In other words, a porous membrane can contain a first plurality of pores with a very small diameter (approximately less than 1 nm) and a second plurality of pores with a very large diameter (approximately greater than 10 micrometers). The larger pore sizes can lead to a higher amount of active material crossover. The ability for a porous membrane to substantially prevent the crossover of active materials can depend on the relative difference in size between the average pore size and the active material. For example, when the active material is a metal center in a coordination compound, the average diameter of the coordination compound can be about 50% greater than the average pore size of the porous membrane. On the other hand, if a porous membrane has substantially uniform pore sizes, the average diameter of the coordination compound can be about 20% larger than the average pore size of the porous membrane. Likewise, the average diameter of a coordination compound is increased when it is further coordinated with at least one water molecule. The diameter of a coordination compound of at least one water molecule is generally considered to be the hydrodynamic diameter. In such embodiments, the hydrodynamic diameter is generally at least about 35% greater than the average pore size. When the average pore size is substantially uniform, the hydrodynamic radius can be about 10% greater than the average pore size.

In some embodiments, the separator can also include reinforcement materials for greater stability. Suitable reinforcement materials can include nylon, cotton, polyesters, crystalline silica, crystalline titania, amorphous silica, amorphous titania, rubber, asbestos, wood or any combination thereof.

Separators within the flow batteries of the present disclosure can have a membrane thickness of less than about 500 micrometers, or less than about 300 micrometers, or less than about 250 micrometers, or less than about 200 micrometers, or less than about 100 micrometers, or less than about 75 micrometers, or less than about 50 micrometers, or less than about 30 micrometers, or less than about 25 micrometers, or less than about 20 micrometers, or less than about 15 micrometers, or less than about 10 micrometers. Suitable separators can include those in which the flow battery is capable of operating with a current efficiency of greater than about 85% with a current density of 100 mA/cm$^2$ when the separator has a thickness of 100 micrometers. In further embodiments, the flow battery is capable of operating at a current efficiency of greater than 99.5% when the separator has a thickness of less than about 50 micrometers, a current efficiency of greater than 99% when the separator has a thickness of less than about 25 micrometers, and a current efficiency of greater than 98% when the separator has a thickness of less than about 10 micrometers. Accordingly, suitable separators include those in which the flow battery is capable of operating at a voltage efficiency of greater than 60% with a current density of 100 mA/cm$^2$. In further embodiments, suitable separators can include those in which the flow battery is capable of operating at a voltage efficiency of greater than 70%, greater than 80% or even greater than 90%.

The diffusion rate of the first and second active materials through the separator can be less than about $1 \times 10^{-5}$ mol cm$^{-2}$ day$^{-1}$, or less than about $1 \times 10^{-6}$ mol cm$^{-2}$ day$^{-1}$, or less than about $1 \times 10^{-7}$ mol cm$^{-2}$ day$^{-1}$, or less than about $1 \times 10^{-9}$ mol cm$^{-2}$ day$^{-1}$, or less than about $1 \times 10^{-11}$ mol cm$^{-2}$ day$^{-1}$, or less than about $1 \times 10^{-13}$ mol cm$^{-2}$ day$^{-1}$, or less than about $1 \times 10^{-15}$ mol cm$^{-2}$ day$^{-1}$.

The flow batteries can also include an external electrical circuit in electrical communication with the first and second electrodes. The circuit can charge and discharge the flow battery during operation. Reference to the sign of the net ionic charge of the first, second, or both active materials relates to the sign of the net ionic charge in both oxidized and reduced forms of the redox active materials under the conditions of the operating flow battery. Further exemplary embodiments of a flow battery provide that (a) the first active material has an associated net positive or negative charge and is capable of providing an oxidized or reduced form over an electric potential in a range the negative operating potential of the system, such that the resulting oxidized or reduced form of the first active material has the same charge sign (positive or negative) as the first active material and the ionomer membrane also has a net ionic charge of the same sign; and (b) the second active material has an associated net positive or negative charge and is capable of providing an oxidized or reduced form over an electric potential in a range of the positive operating potential of the system, such that the resulting oxidized or reduced form of the second active material has the same charge sign (positive or negative sign) as the second active material and the ionomer membrane also has a net ionic charge of the same sign; or both (a) and (b). The matching charges of the first and/or second active materials and the ionomer membrane can provide a high selectivity. More specifically, charge matching can provide less than about 3%, less than about 2%, less than about 1%, less than about 0.5%, less than about 0.2%, or less than about 0.1% of the molar flux of ions passing through the ionomer membrane as being attributable to the first or second active material. The term "molar flux of ions" will refer to the amount of ions passing through the ionomer membrane, balancing the charge associated with the flow of external electricity/electrons. That is, the flow battery is capable of operating or operates with the substantial exclusion of the active materials by the ionomer membrane.

Flow batteries incorporating the electrolyte solutions of the present disclosure can have one or more of the following operating characteristics: (a) where, during the operation of the flow battery, the first or second active materials comprise less than about 3% of the molar flux of ions passing through the ionomer membrane; (b) where, the round trip current efficiency is greater than about 70%, greater than about 80%, or greater than about 90%; (c) where the round trip current efficiency is greater than about 90%; (d) where the sign of the net ionic charge of the first, second, or both active materials is the same in both oxidized and reduced forms of the active materials and matches that of the ionomer membrane; (e) where the ionomer membrane has a thickness of less than about 100 µm, less than about 75 µm, less than about 50 µm, or less than about 250 µm; (f) where the flow battery is capable of operating at a current density of greater than about 100 mA/cm² with a round trip voltage efficiency of greater than about 60%; and (g) where the energy density of the electrolyte solutions is greater than about 10 Wh/L, greater than about 20 Wh/L, or greater than about 30 Wh/L.

In some cases, a user may desire to provide higher charge or discharge voltages than available from a single battery cell. In such cases, several battery cells can be connected in series such that the voltage of each cell is additive. This forms a bipolar stack. An electrically conductive, but non-porous material (e.g., a bipolar plate) can be employed to connect adjacent battery cells in a bipolar stack, which allows for electron transport but prevents fluid or gas transport between adjacent cells. The positive electrode compartments and negative electrode compartments of individual cells can be fluidically connected via common positive and negative fluid manifolds in the stack. In this way, individual cells can be stacked in series to yield a voltage appropriate for DC applications or conversion to AC applications.

In additional embodiments, the cells, cell stacks; or batteries can be incorporated into larger energy storage systems, suitably including piping and controls useful for operation of these large units. Piping, control, and other equipment suitable for such systems are known in the art, and can include, for example, piping and pumps in fluid communication with the respective chambers for moving electrolyte solutions into and out of the respective chambers and storage tanks for holding charged and discharged electrolytes. Any of these locations can be suitable for deploying a solid buffer material in accordance with the embodiments of the present disclosure. The cells, cell stacks, and batteries of this disclosure can also include an operation management system. The operation management system can be any suitable controller device, such as a computer or microprocessor, and can contain logic circuitry that sets operation of any of the various valves, pumps, circulation loops, and the like.

In more specific embodiments, a flow battery system can include a flow battery (including a cell or cell stack) storage tanks and piping for containing and transporting the electrolyte solutions; control hardware and software (which may include safety systems); and a power conditioning unit. The flow battery cell stack accomplishes the conversion of charging and discharging cycles and determines the peak power. The storage tanks contain the positive and negative active materials, and the tank volume determines the quantity of energy stored in the system. The control software, hardware, and optional safety systems suitably include sensors, mitigation equipment and other electronic/hardware controls and safeguards to ensure safe, autonomous, and efficient operation of the flow battery system. A power conditioning unit can be used at the front end of the energy storage system to convert incoming and outgoing power to a voltage and current that is optimal for the energy storage system or the application. For the example of an energy storage system connected to an electrical grid, in a charging cycle the power conditioning unit can convert incoming AC electricity into DC electricity at an appropriate voltage and current for the cell stack. In a discharging cycle, the stack produces DC electrical power and the power conditioning unit converts it to AC electrical power at the appropriate voltage and frequency for grid applications.

Where not otherwise defined hereinabove or understood by one having ordinary skill in the art, the definitions in the following paragraphs will be applicable to the present disclosure.

As used herein, the term "energy density" will refer to the amount of energy that can be stored, per unit volume, in the active materials. Energy density refers to the theoretical energy density of energy storage and can be calculated by Equation 1:

$$\text{Energy density} = (26.8 \text{ A-h/mol}) \times OCV \times [e^-] \quad (1)$$

where OCV is the open circuit potential at 50% state of charge, (26.8 A-h/mol) is Faraday's constant, and $[e^-]$ is the concentration of electrons stored in the active material at 99% state of charge. In the case that the active materials largely are an atomic or molecular species for both the positive and negative electrolyte, $[e^-]$ can be calculated by Equation 2 as:

$$[e^-] = [\text{active materials}] \times N/2 \quad (2)$$

where [active materials] is the molar concentration of the active material in either the negative or positive electrolyte, whichever is lower, and N is the number of electrons transferred per molecule of active material. The related term "charge density" will refer to the total amount of charge that each electrolyte contains. For a given electrolyte, the charge density can be calculated by Equation 3

$$\text{Charge density} = (26.8 \text{ A-h/mol}) \times [\text{active material}] \times N \quad (3)$$

where [active material] and N are as defined above.

As used herein, the term "current density" will refer to the total current passed in an electrochemical cell divided by the geometric area of the electrodes of the cell and is commonly reported in units of mA/cm².

As used herein, the term "current efficiency" ($I_{eff}$) can be described as the ratio of the total charge produced upon discharge of a cell to the total charge passed during charging. The current efficiency can be a function of the state of charge of the flow battery. In some non-limiting embodiments, the current efficiency can be evaluated over a state of charge range of about 35% to about 60%.

As used herein, the term "voltage efficiency" can be described as the ratio of the observed electrode potential, at a given current density, to the half-cell potential for that electrode (×100%). Voltage efficiencies can be described for a battery charging step, a discharging step, or a "round trip voltage efficiency." The round trip voltage efficiency ($V_{eff,RT}$) at a given current density can be calculated from the cell voltage at discharge ($V_{discharge}$) and the voltage at charge ($V_{charge}$) using equation 4:

$$V_{eff,RT} = V_{discharge}/V_{charge} \times 100\% \quad (4)$$

As used herein, the terms "negative electrode" and "positive electrode" are electrodes defined with respect to one another, such that the negative electrode operates or is designed or intended to operate at a potential more negative than the positive electrode (and vice versa), independent of the actual potentials at which they operate, in both charging and discharging cycles. The negative electrode may or may not actually operate or be designed or intended to operate at a negative potential relative to a reversible hydrogen electrode. The negative electrode is associated with a first electrolyte solution and the positive electrode is associated with a second electrolyte solution, as described herein. The electrolyte solutions associated with the negative and positive electrodes may be described as negolytes and posolytes, respectively.

Although the disclosure has been described with reference to the disclosed embodiments, those skilled in the art will readily appreciate that these are only illustrative of the disclosure. It should be understood that various modifications can be made without departing from the spirit of the disclosure. The disclosure can be modified to incorporate any number of variations, alterations, substitutions or equivalent arrangements not heretofore described, but which are commensurate with the spirit and scope of the disclosure. Additionally, while various embodiments of the disclosure have been described, it is to be understood that aspects of the disclosure may include only some of the described embodiments. Accordingly, the disclosure is not to be seen as limited by the foregoing description.

What is claimed is the following:

1. A flow battery comprising:
a first half-cell having a first electrolyte solution therein, the first electrolyte solution comprising a coordination compound having at least one redox non-innocent ligand coordinated to a metal center,
wherein the at least one redox non-innocent ligand bears a quinone functional group,
wherein the quinone functional group is part of an aromatic ring bearing a catechol group, fused to the aromatic ring bearing the catechol group, or tethered via a linker to the aromatic ring bearing the catechol group.

2. The flow battery of claim 1, wherein the at least one redox non-innocent ligand comprises a salt of a substituted catecholate bearing the quinone functional group.

3. The flow battery of claim 1, wherein the at least one redox non-innocent ligand is selected from the group consisting of

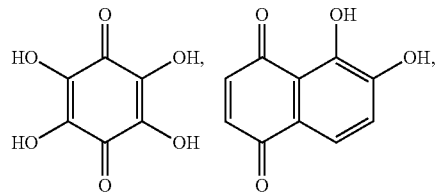

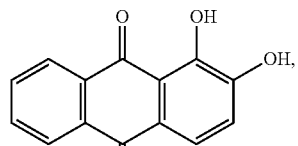

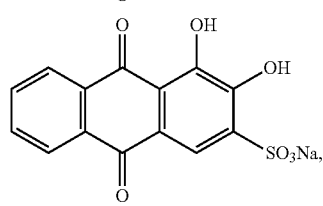

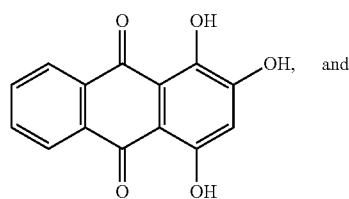

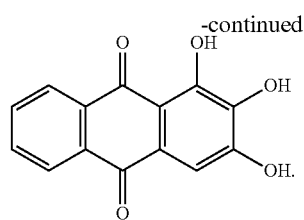

4. The flow battery of claim 1, wherein the coordination compound has a formula of $$D_gM(L_1)(L_2)(L_3);$$

wherein M is a transition metal; D is ammonium, tetraalkylammonium, or an alkali metal ion; g ranges between 0 and 6; and $L_1$, $L_2$ and $L_3$ are ligands, at least one of $L_1$, $L_2$ and $L_3$ being the at least one redox non-innocent ligand.

5. The flow battery of claim 4, wherein the transition metal comprises titanium.

6. The flow battery of claim 1, wherein the metal center comprises a transition metal.

7. The flow battery of claim 6, wherein the transition metal comprises titanium.

8. The flow battery of claim 1, further comprising:
a second half-cell having a second electrolyte solution therein, the second electrolyte solution comprising an iron hexacyanide complex.

9. A composition comprising:
a coordination compound having at least one redox non-innocent ligand coordinated to a metal center;
wherein the at least one redox non-innocent ligand comprises a substituted catecholate or a salt thereof bearing a quinone functional group;
wherein the quinone functional group is part of an aromatic ring bearing a catechol group, fused to the aromatic ring bearing the catechol group, or tethered via a linker to the aromatic ring bearing the catechol group.

10. The composition of claim 9, wherein the metal center comprises a transition metal.

11. The composition of claim 10, wherein the metal center comprises a transition metal.

12. The composition of claim 9, wherein the coordination compound has a formula of $$D_gM(L_1)(L_2)(L_3);$$

wherein M is a transition metal; D is ammonium, tetraalkylammonium, or an alkali metal ion; g ranges between 0 and 6; and $L_1$, $L_2$ and $L_3$ are ligands, at least one of $L_1$, $L_2$ and $L_3$ being the at least one redox non-innocent ligand.

13. The composition of claim 9, wherein the at least one redox non-innocent ligand is selected from the group consisting of

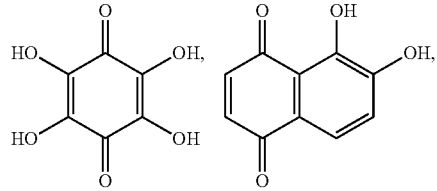

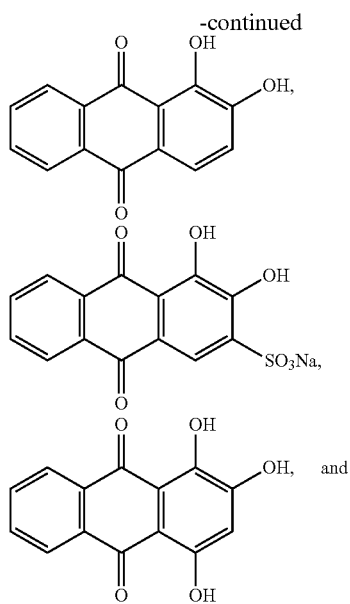
14. The composition of claim 9, further comprising:
an aqueous solution in which the coordination compound is disposed.
15. The composition of claim 14, wherein the aqueous solution has an alkaline pH.
* * * * *